(12) United States Patent
Yamada et al.

(10) Patent No.: US 6,710,043 B1
(45) Date of Patent: Mar. 23, 2004

(54) AMIDE COMPOUNDS

(75) Inventors: Akira Yamada, Fujiidera (JP); Satoshi Aoki, Ibaraki (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/869,962

(22) PCT Filed: Jan. 6, 2000

(86) PCT No.: PCT/JP00/00017

§ 371 (c)(1),
(2), (4) Date: Jul. 10, 2001

(87) PCT Pub. No.: WO00/42011

PCT Pub. Date: Jul. 20, 2000

(30) Foreign Application Priority Data

Jan. 14, 1999 (AU) ............................................. PP8180

(51) Int. Cl.[7] .............................................. A01N 43/62
(52) U.S. Cl. ...................................................... 514/218
(58) Field of Search ............................ 546/224; 514/329

(56) References Cited

U.S. PATENT DOCUMENTS

| | | | | |
|---|---|---|---|---|
| 3,647,805 A | 3/1972 | Irikura et al. | ............... | 546/224 |
| 5,346,907 A | 9/1994 | Kerwin et al. | ............... | 514/312 |
| 5,723,490 A | 3/1998 | Tung | ............... | 514/478 |
| 6,344,358 B1 * | 2/2002 | Matsuoka et al. | ............. | 436/63 |

FOREIGN PATENT DOCUMENTS

| | | |
|---|---|---|
| CA | 2 077 252 | 3/1994 |
| DE | 19 38 512 | 1/1971 |
| DE | 23 11 570 | 9/1973 |
| DE | 22 40 665 | 3/1974 |
| DE | 25 45 501 | 4/1976 |
| EP | 0 002 401 | 6/1979 |
| EP | 0 255 134 | 2/1988 |
| EP | 0 299 493 | 1/1989 |
| EP | 0 308 337 | 3/1989 |
| EP | 0 436 734 | 7/1991 |
| EP | 0 625 507 | 11/1994 |
| EP | 0 628 310 | 12/1994 |
| EP | 0 700 913 | 6/1996 |
| WO | WO 94/22826 | 10/1994 |
| WO | WO 96/31501 | 10/1996 |
| WO | WO 97/11069 | 3/1997 |
| WO | WO 97/17957 | 5/1997 |
| WO | WO 97/28141 | 8/1997 |
| WO | WO 98/25914 | 6/1998 |
| WO | WO 98/27930 | 7/1998 |
| WO | WO 98/35951 | 8/1998 |

OTHER PUBLICATIONS

Search result of 37 references with RN delineation before 1998.*
Archibald et al. "antiinflammatory . . . " CA 72:121363 (1969).*
Jullien et al. "functional derivatives . . . " CA 74:99888 (1970).*
Pomaret et al. "10–pheylthiazinyl . . . " CA 74:42381 (1969).*

* cited by examiner

*Primary Examiner*—Ceila Chang
(74) *Attorney, Agent, or Firm*—Oblon, Spivak, McClelland, Maier & Neustadt, P.C.

(57) ABSTRACT

This invention relates to amide compounds having the potentiation of the cholinergic activity and represented by formula (I)

$$R^1-A-N\overset{E}{\underset{R^3}{\diagup\diagdown}}\underset{R^4}{X}-Y-Q-R^2 \quad (I)$$

wherein $R^1$ is acyl, $R^2$ is lower alkyl, A is a single bond, —CO— or —SO$_2$—, E is lower alkylene, X is CH or N, Y is a single bond, Q is —CH$_2$— etc. and $R^3$ and $R^4$ are taken together to form lower alkylene etc., pharmaceutically acceptable salts and processes fro preparation thereof and a pharmaceutical composition comprising the same.

7 Claims, No Drawings

AMIDE COMPOUNDS

TECHNICAL FIELD

This invention relates to new amide compounds and pharmaceutically acceptable salts thereof which are useful as a medicament.

BACKGROUND ART

Some aminopiperazine derivatives have been known as useful anti-amnesia or anti-dementia agents, for example, in PCT International Publication Nos. WO 91/01979 and WO 98/35951.

DISCLOSURE OF INVENTION

This invention relates to new amide compounds and pharmaceutically acceptable salts thereof.

More particularly, it relates to new amide compounds and pharmaceutically acceptable salts thereof which have the potentiation of the cholinergic activity, to processes for the preparation thereof, to a pharmaceutical composition comprising the same, and to a method for the treatment and/or prevention of disorders in the central nervous system for mammals, and more particularly to method for the treatment and/or prevention of amnesia, dementia (e.g., senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, etc.), and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

One object of this invention is to provide new and useful amide compounds and pharmaceutically acceptable salts thereof which possess the potentiation of the cholinergic activity.

Another object of this invention is to provide processes for preparation of said amide compounds and salts thereof.

A further object of this invention is to provide a pharmaceutical composition comprising, as an active ingredient, said amide compounds and pharmaceutically acceptable salt thereof.

Still further object of this invention is to provide a therapeutic method for the treatment and/or prevention of aforesaid diseases in mammals, using said amide compounds and pharmaceutically acceptable salts thereof.

The amide compounds of this invention are new and can be represented by the following general formula [I]:

(I)

wherein $R^1$ is acyl, $R^2$ is lower alkyl, lower alkoxy, lower alkylamino, lower alkenyl, lower alkenyloxy, lower alkenylamino, lower alkynyl, lower alkynyloxy, lower alkynylamino, cyclo(lower)alkyl, cyclo(lower)alkyloxy, cyclo(lower)alkylamino, aryl, aryloxy, arylamino, a heterocyclic group or amino substituted with a heterocyclic group, each of which may be substituted with suitable substituent(s); or acyl;

A is a single bond,

or $—SO_2—$,

E is lower alkylene optionally substituted with suitable substituent(s),

X is CH or N,

Y is a single bond, lower alkylene or

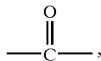

wherein $R^5$ is hydrogen, lower alkyl, substituted-lower alkyl, an N-protective group, aryl, acyl or a heterocyclic group), Q is $—CH_2—$,

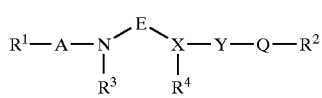

$—SO_2—$ or $—N=CH—$, and $R^3$ and $R^4$ are each hydrogen or lower alkyl, or are taken together to form lower alkylene optionally condensed with a cyclic hydrocarbon or a heterocyclic ring, provided that when X is N, then 1) Y is a single bond, and
Q is $—CH_2—$,

or $—SO_2—$, or

2) Y is lower alkylene, and pharmaceutically acceptable salts thereof. The object compound [I] or its salt can be prepared by processes as illustrated in the following reaction schemes.

Process 1

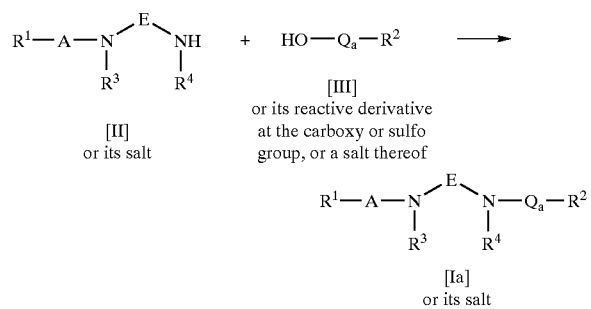

[II]
or its salt

[III]
or its reactive derivative
at the carboxy or sulfo
group, or a salt thereof

[Ia]
or its salt

Process 2
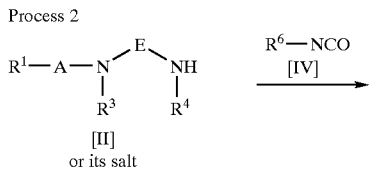
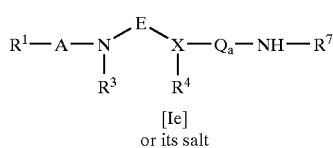
Process 7
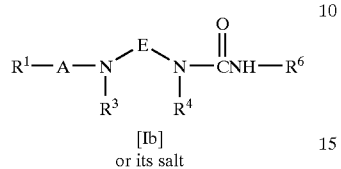
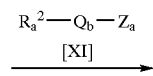
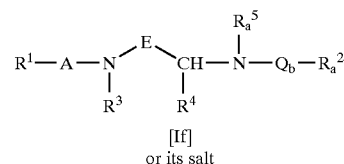
Process 3
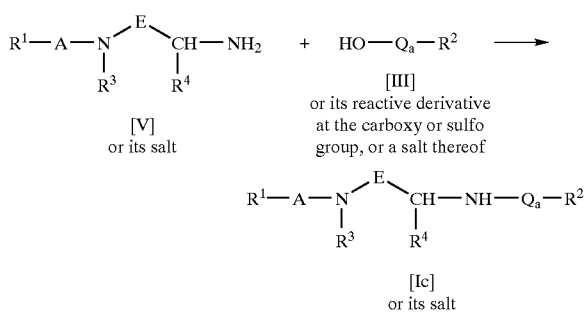
Process 8
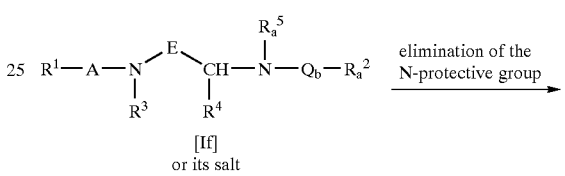
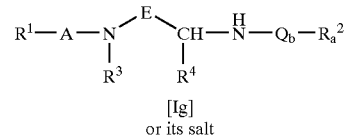
Process 4
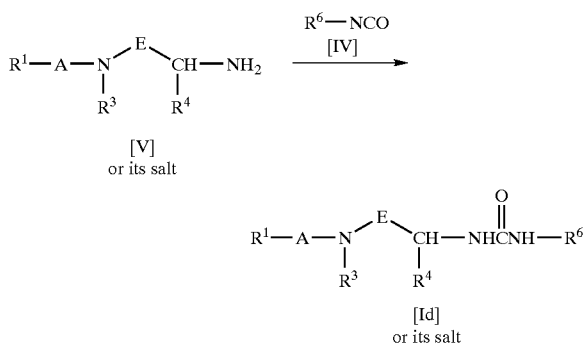
Process 9
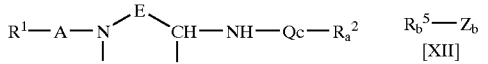
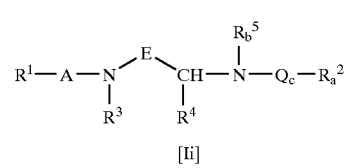
Process 5
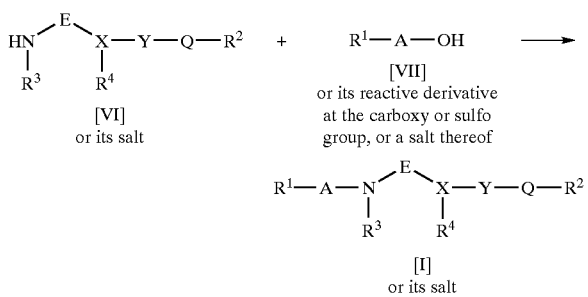
Process 10
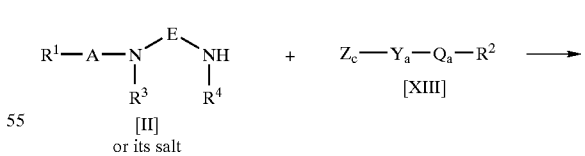
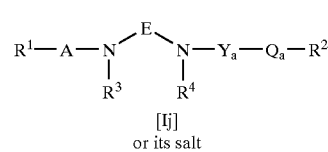
Process 6
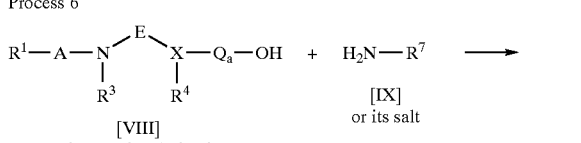
wherein $R^1$, $R^2$, $R^3$, $R^4$, A, E, Q, X and Y are each as defined above, $Q_a$ is

or —SO$_2$—,

R$^6$ is aryl which may be substituted with suitable substituent(s), or pyridyl, R$^7$ is lower alkyl, lower alkenyl, lower alkynyl, cyclo(lower)alkyl, aryl or a heterocyclic group, each of which may be substituted with suitable substituent(s), R$_a^5$ is an N-protective group, R$_a^2$ is lower alkyl, lower alkenyl, lower alkynyl, cyclo(lower)alkyl, aryl or a heterocyclic group, each of which may be substituted with suitable substituent(s), $Q_b$ is —CH$_2$—,

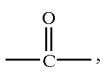

or —SO$_2$—, $Z_a$ is an acid residue, $Q_c$ is

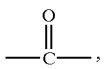

R$_b^5$ is lower alkyl, $Z_b$ is an acid residue, $Z_c$ is an acid residue, and $Y_a$ is lower alkylene.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The lower moiety in the term "lower alkenyl", "lower alkenyloxy", "lower alkenylamino", "lower alkynyl", "lower alkynyloxy" and "lower alkynylamino" is intended to mean a group having 2 to 6 carbon atoms.

The lower moiety in the terms "cyclo(lower)alkyl", "cyclo(lower)alkyloxy" and "cyclo(lower)alkylamino" is intended to mean a group having 3 to 6 carbon atoms.

Suitable "lower alkyl" and lower alkyl moiety in the terms "substituted-lower alkyl", "ar(lower)alkyl", "halo(lower)alkyl", "lower alkylamino", "lower alkylsilyl", "lower alkylthio" and "lower alkylsulfonyl" may be a straight or branched C$_1$–C$_6$ alkyl such as methyl, ethyl, propyl, isopropyl, butyl, isobutyl, tert-butyl, pentyl, ethylpropyl, hexyl or the like, in which preferable one is methyl.

Suitable "lower alkenyl" and lower alkenyl moiety in the terms "lower alkenyloxy" and "lower alkenylamino" may be a straight or branched C$_2$–C$_6$ alkenyl such as ethenyl, propenyl, butenyl, pentenyl, hexenyl, isopropenyl, butadienyl, pentadienyl, hexadienyl or the like, in which preferable one is ethenyl, propentyl or butadienyl.

Suitable "lower alkynyl" and lower alkynyl moiety in the terms "lower alkynyloxy" and "lower alkynylamino" may be a straight or branched C$_2$–C$_6$ alkynyl such as ethynyl, propargyl, butynyl or the like, in which preferable one is ethynyl.

Suitable "cyclo(lower)alkyl" and cyclo(lower)alkyl moiety in the terms "cyclo(lower)alkyloxy" and "cyclo(lower)alkylamino" may be cyclo(C$_3$–C$_6$)alkyl such as cyclopropyl, cyclobutyl, cyclopentyl or cyclohexyl, in which preferable one is cyclopropyl.

Suitable "aryl" and aryl or ar moiety in the terms "ar(lower)alkoxy", "aryloxy", "arylamino", "arylsulfonyl", "aroyl" and "ar(lower)alkyl" may be phenyl, naphthyl, phenyl substituted with lower alkyl [e.g. tolyl, xylyl, mesityl, cumenyl, di(tert-butyl)phenyl, etc.] and the like, in which preferable one is phenyl or tolyl.

Suitable "ar(lower)alkyl" may be benzyl, phenethyl, phenylpropyl, benzhydryl, trityl and the like, in which preferable one is benzyl.

Suitable "lower alkylene" and lower alkylene moiety in the term "lower alkylenedioxy" may be a straight or branched C$_1$–C$_6$ alkylene such as methylene, ethylene, trimethylene, propylene, tetramethylene, pentamethylene, hexamethylene, ethylethylene or the like, in which preferable one is methylene, ethylene or trimethylene.

Suitable "lower alkoxy" and lower alkoxy moiety in the terms "ar(lower)alkoxy" and "halo(lower)alkoxy" may be a straight or branched C$_1$–C$_6$ alkoxy such as methoxy, ethoxy, propoxy, isopropoxy, methylpropoxy, butoxy, isobutoxy, tert-butoxy, pentyloxy, hexyloxy or the like, in which preferable one is methoxy or tert-butoxy.

Suitable "ar(lower)alkoxy" may be benzyloxy, phenethyloxy, phenylpropyloxy, benzhydryloxy, trityloxy and the like.

Suitable "halogen" and halo moiety in the term "halo(lower)alkyl" may be fluorine, chlorine, bromine and iodine, in which preferable one is fluorine, chlorine or iodine.

Suitable "halo(lower)alkyl" may be lower alkyl substituted with one or more halogens such as chloromethyl, dichloromethyl, fluoromethyl, difluoromethyl, trifluoromethyl, pentachloroethyl or the like, in which preferable one is trifluoromethyl.

Suitable "halo(lower)alkoxy" may be lower alkoxy substituted with one or more halogens such as chloromethoxy, dichloromethoxy, fluoromethoxy, difluoromethoxy, trifluoromethoxy, pentachloromethoxy or the like, in which preferable one is trifluoromethoxy.

Suitable "lower alkylamino" may be mono or di (lower alkylamino) such as methylamino, ethylamino, porpylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is dimethylamino.

Suitable "lower alkylsilyl" may be mono, di, or tri(lower)alkylsilyl such as trimethylsilyl, dimethylsilyl, triethylsilyl or the like, in which preferable one is trimethylsilyl.

Suitable "lower alkylenedioxy" may be methylenedioxy, ethylenedioxy and the like, in which preferable one is methylenedioxy.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 7-membered heteromonocyclic group containing 1 to 4 nitrogen atoms [e.g. pyrrolidinyl, imidazolidinyl, piperidyl, piperazinyl, homopiperazinyl, etc.]; unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolo-pyridazinyl [e.g. tetrazolo[1,5-b]pyridazinyl, etc.], quioxalinyl, etc.;

unsaturated 3 to 6-membered heteromonocyclic group containing an oxygen atom, for example, pyranyl, furyl, etc.;

saturated 3 to 6-membered heteromonocyclic group containing an oxygen atom, for example, 1H-tetrahydropyranyl, tetrahydrofuranyl, etc.;

unsaturated 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 2-oxazolinyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzofurazanyl, benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g. thiazolidinyl, etc.];

unsaturated condensed heterocyclic group containing 1 to 2 sulfur atoms and 1 to 3 nitrogen atoms [e.g. benzothiazolyl, benzothiadiazolyl, etc.];

unsaturated condensed heterocyclic group containing 1 to 2 oxygen atoms [e.g. benzofuranyl, benzodioxolyl, chromanyl, etc.] and the like.

Said "heterocyclic group" may be substituted with lower alkyl as exemplified above, in which preferable one is thienyl, pyridyl, methylpyridyl, quinolyl, indolyl, quinoxalinyl, benzofuranyl or tetramethylchromanyl, and more preferable one is pyridyl.

Suitable "acyl" may be carboxy; esterified carboxy;

carbamoyl substituted with lower alkyl, aryl, ar(lower)alkyl, arylsulfonyl, lower alkylsulfonyl or a heterocyclic group;

substituted or unsubstituted arylsulfonyl;

lower alkylsulfonyl; cyclo(lower)alkylcarbonyl;

lower alkanoyl; substituted or unsubstituted aroyl;

a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is unsubstituted lower alkoxycarbonyl and more preferable one is methoxycarbonyl or tert-butoxycarbonyl.

The carbamoyl substituted with lower alkyl may be methylcarbamoyl, ethylcarbamoyl, propylcarbamoyl, dimethylcarbamoyl, diethylcarbamoyl, N-methyl-N-ethylcarbamoyl and the like.

The carbamoyl substituted with aryl may be phenylcarbamoyl, naphthylcarbamoyl, lower alkyl-substituted phenylcarbamoyl [e.g. tolylcarbamoyl, xylylcarbamoyl, etc.] and the like.

The carbamoyl substituted with ar(lower)alkyl may be benzylcarbamoyl, phenethylcarbamoyl, phenylpropylcarbamoyl and the like, in which preferable one is benzylcarbamoyl.

The carbamoyl substituted with arylsulfonyl may be phenylsulfonylcarbamoyl, tolylsulfonylcarbamoyl and the like.

The carbamoyl substituted with lower alkylsulfonyl may be methylsulfonylcarbamoyl, ethylsulfonylcarbamoyl and the like.

The carbamoyl substituted with a heterocyclic group may be one substituted with a heterocyclic group as mentioned above.

The lower alkanoyl may be formyl, acetyl, propionyl, butyryl, isobutyryl, valeryl, isovaleryl, pivaloyl, hexanoyl and the like, in which preferable one is acetyl or pivaloyl.

The substituted or unsubstituted aroyl may be benzoyl, naphthoyl, toluoyl, di(tert-butyl)benzoyl, halo(lower)alkoxybenzoyl [e.g. trifluoromethoxybenzoyl, etc.] and the like, in which preferable one is benzoyl or trifluoromethoxybenzoyl.

The substituted or unsubtituted arylsulfonyl may be phenylsulfonyl, tolylsulfonyl, halophenylsulfonyl [e.g. fluorophenylsulfonyl, etc.] and the like, in which preferable one is fluorophenylsulfonyl.

The lower alkylsulfonyl may be methylsulfonyl, ethylsulfonyl and the like, in which preferable one is methylsulfonyl.

The cyclo(lower)alkylcarbonyl may be cyclo($C_3$–$C_6$)-alkylcarbonyl such as cyclopropylcarbonyl, cyclobutylcarbonyl, cyclopentylcarbonyl or cyclohexylcarbonyl, in which preferable one is cyclopropylcarbonyl.

The heterocyclic moiety in the term "a heterocycliccarbonyl" may be one mentioned above as a heterocyclic group.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "N-protective group" may be common N-protective group such as substituted or unsubstituted lower alkanoyl [e.g. formyl, acetyl, propionyl, trifluoroacetyl, etc.], lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], 9-fluorenylmethoxycarbonyl, substituted or unsubstituted arenesulfonyl [e.g. benzenesulfonyl, tosyl, etc.], nitrophenylsulfenyl, aralkyl [e.g. trityl, benzyl, etc.] or the like, in which preferable one is lower alkoxycarbonyl and more preferable one is tert-butoxycarbonyl.

Suitable "cyclic hydrocarbon" may be a saturated or unsaturated cyclic hydrocarbon such as cyclopentane, cyclohexane, benzene, naphthalene, indan, indene or the like.

Suitable "substituted-lower alkyl" may be lower alkyl substituted with halogen, aryl, acyl, lower alkoxy, aryloxy and the like, in which preferable one is benzyl.

Suitable "heterocyclic ring" may be one which is a heterocyclic group, as mentioned above, added by hydrogen.

Preferred "acyl" for $R^1$ may be lower alkanoyl; lower alkoxycarbonyl; aroyl optionally substituted with halo(lower)alkoxy; arylsulfonyl optionally substituted with halogen; lower alkylsulfonyl; or cyclo(lower)alkylcarbonyl, in which more preferable one is acetyl, pivaloyl, methoxycarbonyl, tert-butoxycarbonyl, benzoyl, trifluoromethoxybenzoyl, fluorophenylsulfonyl, methylsulfonyl or cyclopropylcarbonyl.

Preferred "suitable substituent" as the substituent of lower alkyl, lower alkoxy, lower alkylamino, lower alkenyl, lower alkenyloxy, lower alkenylamino, lower alkynyl, lower alkynyloxy, lower alkynylamino, cyclo(lower)alkyl, cyclo(lower)alkyloxy, cyclo(lower)alkylamine, aryl, aryloxy, arylamino, a heterocyclic group or amino substituted a heterocyclic group for $R^2$ may be halo(lower)alkyl, halo(lower)alkoxy, lower alkenyl, lower alkynyl, lower alkylamino, acylamino, acyl, lower alkylsilyl, lower alkoxy, aryl, lower alkylenedioxy, acyloxy, hydroxy, nitro, amino, cyano, halogen, aryloxy, lower alkylthio and the like.

Preferred "aryl which may be substituted with suitable substituent(s)" for $R^2$ may be aryl optionally substituted with halogen, in which more preferable one is fluorophenyl.

Preferred "arylamino which may be substituted with suitable substituent(s)" for $R^2$ may be arylamino optionally substituted with halogen, in which preferable one is phenylamino or fluorophenylamino.

Preferred "aryloxy which may be substituted with suitable substituent(s)" for $R^2$ may be aryloxy optionally substituted with halogen, in which preferable one is fluorophenoxy.

Preferred "lower alkylene" for Y may be methylene.

Preferred "lower alkyl" for $R^5$ in Y may be methyl.

Preferred "N-protective group" for $R^5$ in Y may be tert-butoxycarbonyl.

Preferred "suitable substituent" as the substituent of lower alkylene for E may be oxo, lower alkyl, hydroxy(lower)alkyl or acyl, in which more preferable one is oxo, dioxo, methyl, dimethyl, hydroxymethyl, or benzylcarbamoyl.

Preferred "lower alkylne" for E may be methylene, ethylene or trimethylene, and more preferable one is ethylene.

Preferred "lower alkyl" for $R^3$ and $R^4$ may be methyl.

Preferred "lower alkylene which $R^3$ and $R^4$ are taken together to form" may be ethylene or trimethylene.

Preferred "a cyclic hydrocarbon with which lower alkylene is condensed" may be benzene.

Preferred compound [I] is one having lower alkanoyl, lower alkoxycarbonyl, aroyl, aroyl substituted with halo(lower)alkoxy, lower alkylsulfonyl, arylsulfonyl, arylsulfonyl substituted with halogen or cyclo(lower)alkylcarbonyl for $R^1$, aryl, aryloxy or arylamino, each aryl of which may be substituted with halogen; pyridyl; or pyridylamino for $R^2$, a single bond for A, ethylene for E, CH for X,

for Y,

for Q, and ethylene for $R^3$ and $R^4$ to be taken together to form, or lower alkanoyl, lower alkoxycarbonyl, aroyl, aroyl substituted with halo(lower)alkoxy, lower alkylsulfonyl, arylsulfonyl, arylsulfonyl substituted with halogen or cyclo(lower)alkylcarbonyl for $R^1$, aryl, aryloxy or arylamino, each aryl of which may be substituted with halogen; pyridyl; or pyridylamino for $R^2$, a single bond for A, ethylene for E, N for X, a single bond for Y,

for Q, and ethylene for $R^3$ and $R^4$ to be taken together to form.

Suitable pharmaceutically acceptable salts of the object compound [I] are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. aspartic acid salt, glutamic acid salt, etc.], a metal salt such as an alkali metal salt [e.g. sodium salt, potassium salt, etc.] and alkaline earth metal salt [e.g. calcium salt, magnesium salt, etc.] and the like.

The processes for preparing the object compound [I] are explained in detail in the following.

Process 1

The compound [Ia] or its salt can be prepared by reacting a compound [II] or its salt with a compound [III] or its reactive derivative at the carboxy or sulfo group, or a salt thereof.

Suitable salts of the compounds [Ia] and [III] may be the same as those exemplified for the compound [I].

Suitable salts of the compound [III] and its reactive derivative at the carboxy or sulfo group may be metal salt or alkaline earth metal salt as exemplified for the compound [I].

Suitable reactive derivative at the carboxy or sulfo group or the compound [III] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.), substituted phosphoric acid [e.g. dialkylphosphoric acid, diphenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxybenzotriazole, 1-hydroxy-6-chloro-1H-benzotriazole, or the like. These reactive derivatives can be optionally selected according to the kind of the compound [III] to be used.

The reaction is usually carried out in a conventional solvent such as water, acetone, dioxane, chloroform, methylene chloride, ethylene dichloride, tetrahydrofuran, acetonitrile, ethyl acetate, N,N-dimethylformamide, pyridine or any other organic solvent which does not adversely influence the reaction. Among these solvents, hydrophilic solvent may be used in a mixture with water.

The reaction is also preferably carried out in the presence of a conventional base such as triethylamine, diisopropylethylamine, pyridine, N,N-dimethylaminopyridine, etc., or a mixture thereof.

When the compound [III] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide (e.g. ethyl chloroformate, isobutyl chloroformate, etc.], 1-(p-chlorobenzenesulfonyloxy)-6-chloro-1H-benzotriazole, or the like.

The reaction temperature is not critical, and the reaction can be carried out under cooling to heating.

Process 2

The compound [Ib] or its salt can be prepared by reacting a compound [III] or its salt with a compound [IV].

Suitable salts of the compounds [Ib] and [II] may be the same as those exemplified for the compound [I].

This reaction is usually carried out in a solvent such as dioxane, tetrahydrofuran, benzene, toluene, chloroform, methylene chloride or any other organic solvent which does not adversely influence the reaction.

The reaction temperature is not critical, and the reaction is usually carried out under cooling to warming.

Process 3

The compound [Ic] or its salt can be prepared by reacting a compound [V] or its salt with a compound [III] or its reactive derivative at the carboxy or sulfo group, or a salt thereof.

Suitable salts of the compounds [Ic] and [V] may be the same as those exemplified for the compound [I].

Suitable salts of the compound [III] and its reactive derivative at the carboxy or sulfo group may be metal salt or alkaline earth metal salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

Process 4

The compound [Id] or its salt can be prepared by reacting a compound [V] or its salt with a compound [IV].

Suitable salts of the compounds [Id] and [V] may be the same as those exemplified for the compound [I].

This reaction can be carried out in substantially the same manner as Process 2, and therefore the reaction mode and reaction condition [e.g. solvent, reaction temperature, etc.] of this reaction are to be referred to those explained in Process 2.

Process 5

The compound [I] or its salt can be prepared by reacting a compound [VI] or its salt with a compound [VII] or its reactive derivative at the carboxy or sulfo group, or a salt thereof.

Suitable salt of the compound [VI] may be acid addition salt as exemplified for the compound [I].

Suitable salts of the compound [VII] and its reactive derivative at the carboxy or sulfo group may be metal salt or alkaline earth metal salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

Process 6

The compound [Ie] or its salt can be prepared by reacting a compound [VIII] or its reactive derivative at the carboxy group or sulfo group, or a salt thereof with a compound [IX] or its salt.

Suitable salts of the compounds [Ie], [VIII] and its reactive derivative at the carboxy or sulfo group may be the same as those exemplified for the compound [I].

Suitable salt of the compound [IX] may be acid addition salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

Process 7

The compound [If] can be prepared by reacting a compound [X] or its salt with a compound [XI].

Suitable salts of the compounds [If] and [X] may be the same as those exemplified for the compound [I].

The present reaction is preferably carried out in the presence of base such as an alkali metal [e.g. lithium, sodium, potassium, etc.], alkaline earth metal [e.g. calcium, etc.], alkali metal hydride [e.g. sodium hydride, etc.], alkaline earth metal hydride [e.g. calcium hydride, etc.], the hydroxide or carbonate or bicarbonate of an alkali metal or an alkaline earth metal [e.g. potassium bicarbonate, etc.] and the like.

This reaction is usually carried out in a solvent such as N,N-dimethylformamide, diethyl ether, tetrahydrofuran, dioxane, benzene, toluene, acetonitrile or any other solvent which does not adversely influence the reaction.

The reaction temperature is not critical, and the reaction is usually carried out under cooling to heating.

Process 8

The object compound [Ig] of its salt can be prepared by subjecting a compound [If] or its salt to elimination reaction of the N-protective group.

Suitable salts of the compounds [If] and [Ig] may be acid addition salts as exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, alkylamine [e.g. methylamine, trimethylamine, triethylamine, etc.], picoline, 1,5-diazabicyclo[4.3.0]non-5-ene, 1,4-diazabicyclo[2.2.2]octane, 1,8-diazabicyclo-[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. richloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, dioxane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the N-protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

Process 9

The compound [Ii] or its salt can be prepared by reacting a compound [Ih] or its salt with a compound [XII].

Suitable salts of the compounds [Ih] and [Ii] may be the same as those exemplified for the compound [I].

This reaction can be carried out in substantially the same manner as Process 7, and therefore the reaction mode and reaction condition [e.g. solvent, reaction temperature, etc.] of this reaction are to be referred to those explained in Process 7.

Process 10

The compound [Ij] or its salt can be prepared by reacting a compound [II] or its salt with a compound [XIII].

Suitable salts of the compounds [Ij] and [II] may be the same as those exemplified for the compound [I].

This reaction can be carried out in substantially the same manner as Process 7, and therefore the reaction mode and reaction condition [e.g. solvent, reaction temperature, etc.] of this reaction are to be referred to those explained in Process 7.

The compounds obtained by the above processes can be isolated and purified by a conventional method such as pulverization, recrystallization, column chromatography, reprecipitation, or the like.

It is to be noted that the compound [I] and the other compounds may include one or more stereoisomer(s) such as optical isomer(s) or geometrical isomer(s) due to asymmetric carbon atom(s) and double bond(s), and all of such isomers and mixture thereof are included within the scope of this invention.

Additionally, it is to be noted that any solvate [e.g. enclosure compound (e.g. hydrate, etc.)] of the compound [I] or a pharmaceutically acceptable salt thereof is also included within the scope of this invention.

The object compound [I] and pharmaceutically acceptable salts thereof possess strong potentiation of the cholinergic activity, and are useful for the treatment and/or prevention of disorders in the central nervous system for mammals, and more particularly of amnesia, dementia (e.g., senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, etc.) and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

In order to illustrate the usefulness of the object compound [I], the pharmacological data of the compound [I] is shown in the following.

Test

Penile Erection in Rat (This test was carried out according to a similar manner to that described in Jpn. J. Pharmacol., Vol. 64, 147–153 (1994))

(i) Method

Male Fischer 344 rats at the age of 8 weeks (n=7) were used. All rats were handled 3 minutes a day for three successive days before the tests. The rats were tested in groups of seven and various doses of the test compound were given in semi-randomized order. The test compounds were suspended in 0.5% methyl-cellulose immediately before use, and given intraperitoneally in a volume of 1 ml/kg just before the start of test. Immediately after injection, each rat was placed in a perspex box (25×25×35 cm) and its behavior was observed for 60 minutes, during which time the number of penile erections was counted. A mirror was situated behind each box to facilate of the rat. Data was expressed as a mean number.

(ii) Test Result

| Test Compound (Example No.) | Dose (mg/kg) | Penile Erection (number/hr) |
|---|---|---|
| 2 | 1 | 1.14 |
| 19 | 0.32 | 0.75 |

It is clear that the compound having the above-mentioned activity ameliorates the memory deficits (i.e. amnesia, dementia, etc.) from the description in the Journal of Pharmacology and Experimental Therapeutics, Vo. 279, No. 3, 1157–1173 (1996). Further, it is expected that the compound having the above-mentioned activity is useful as therapeutical and/or preventive agent for aforesaid diseases from some patent applications (e.g. PCT International Publication No. WO 98/27930, etc.).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral or parenteral administration. The pharmaceutical preparations may be capsules, tablets, dragees, granules, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

To a solution of 1-benzyl-4-aminopiperidine (50 g) in water (360 ml) was added a solution of di-tert-butyl dicarbonate (61 g) in acetone (360 ml) dropwise under cooling on an ice-water bath. After stirring for 2.5 hours, a precipitate was collected on a filter, washed with water, and dried. The crude product was poured into a mixture of diisopropyl ether (200 ml) and n-hexane (200 ml) and the mixture was stirred. After filtration, O-tert-butyl N-(1-benzylpiperidin-4-yl)carbamate (66.9 g) was obtained.

NMR (DMSO-$d_6$, $\delta$): 1.2–1.5 (2H, m), 1.37 (9H, s), 1.66 (2H, br d, J=9.9 Hz), 1.91 (2H, br t, J=10.7 Hz), 2.73 (2H, distorted d, J=11.8 Hz), 3.2 (1H, m), 3.41 (2H, s), 6.75 (1H, d, J=7.8 Hz), 7.1–7.4 (5H, m); MASS (APCI)(m/z): 291.

Preparation 2

To a mixture of O-tert-butyl N-(1-benzylpiperidin-4-yl) carbamate. (45 g) and 10% palladium on carbon (50% wet, 9 g) in methanol (1l) was bubbled hydrogen gas under stirring at ambient temperature. The catalyst was removed by glass filter and the solvent was removed under reduced pressure. After rinse with diisopropyl ether, O-tert-butyl N-(piperidin-4-yl)carbamate (28.35 g) was obtained. The washed solvent was removed under reduced pressure, and the residue was rinsed with diisopropyl ether. The second fraction of O-tert-butyl N-(piperidin-4-yl)carbamate (344 mg) was obtained.

NMR (DMSO-$d_6$, $\delta$): 1.18 (2H, ddd, J=3.8, 11.8, 11.8 Hz), 1.37 (9H, s), 1.62 (2H, distorted d, J=10.8 Hz), 1.85 (1H, m), 2.38 (2H, dt, J=2.2, 12.0 Hz), 2.86 (2H, distorted d, J=12.3 Hz), 3.2 (1H, m), 6.72 (1H, br d); MASS (APCI) (m/z): 201.

Preparation 3

To a suspension of O-tert-butyl N-(piperidin-4-yl) carbamate (4.0 g) in dichloromethane (40 ml) were added pyridine (1.94 ml), dichloromethane (40 ml), acetic anhydride (20.8 ml) and then N,N-dimethylaminopyridine (0.1 g) at ambient temperature. After stirring for 3 hours, the mixture was washed with 0.1N hydrochloric acid, water, and brine. After drying with magnesium sulfate, the solvents were removed under reduced pressure. After rinse with diisopropyl ether, O-tert-butyl N-(1-acetylpiperidin-4-yl) carbamate (4.01 g) was obtained.

NMR (DMSO-$d_6$, $\delta$): 1.23 (2H, m), 1.38 (9H, s), 1.70 (2H, distorted t, J=11.4 Hz), 1.97 (3H, s), 2.64 (1H, br t, J=11.1Hz), 3.04 (1H, dt, J=2.8, 11.5 Hz), 3.42 (1H, m), 3.72 (1H, br d, J=15.0 Hz), 4.19 (1H, br d, J=13.1 Hz), 6.86 (1H, d, J=7.5 Hz); MASS (APCI)(m/z): 243.

Preparation 4

To a solution of O-tert-butyl N-(1-acetylpiperidin-4-yl) carbamate (2.42 g) in dichloromethane (24 ml) was added 4N hydrogen chloride in dioxane (24 ml). The solvents were removed under reduced pressure. After rinse with diisopropyl ether, 1-acetyl-4-aminopiperidine hydrochloride (2.02 g) was obtained.

NMR (DMSO-$d_6$, $\delta$): 1.41 (2H, m), 1.93 (2H, distorted t), 2.00 (3H, s), 2.60 (1H, br t, J=10.4 Hz), 3.06 (1H, br t, J=11.3 Hz), 3.12 (1H, m), 3.84 (1H, br d, J=14.0 Hz), 4.34 (1H, br d, J=13.0 Hz), 8.32 (3H, br s); MASS (APCI)(m/z): 143.

Preparation 5

To a solution of phenyl chloroformate (5.64 g) in dichloromethane (70 ml) was added a solution of 4-aminopyridine (2.84 g) and triethylamine (5.02 ml) in dichloromethane (100 ml) dropwise under cooling on an ice-water bath. After stirring for 1 hour, the solvents were removed under reduced pressure. A residue was diluted with dichloromethane (200 ml) and water (200 ml). An organic phase was separated and washed with water and brine. After drying with magnesium sulfate, the solvents were removed under reduced pressure. The reaction mixture was diluted with diisopropyl ether and the precipitates were filtered. After rinse with diethyl ether, O-phenyl N-(4-pyridyl)carbamate (5.07 g) was obtained.

NMR (CDCl$_3$, $\delta$): 7.17 (2H, m), 7.27 (1H, m), 7.3–7.5 (4H, m), 8.50 (2H, dd, J=1.4, 5.0 Hz), 8.06 (1H, s); MASS (APCI)(m/z): 215.

Preparation 6

A solution of sulfuryl chloride (3.55 ml) in chloroform (45 ml) was added a solution of 1-acetylpiperazine (5.66 mg) and triethylamine (6.16 ml) in chloroform (15 ml) dropwise under cooling on an ice-water bath. After stirring for 6 hours, a precipitate was collected by filtration. After drying over sodium hydroxide, 1-acetylpiperazine-4-sulfonyl chloride (2.43 g) was obtained.

NMR (CDCl$_3$, δ): 2.15 (3H, s), 3.35 (4H, m), 3.69 (2H, t, J=5.1 Hz), 3.83 (2H, br s); MASS (APCI)(m/z): 227.

Preparation 7

To a solution of 1-benzyl-4-aminopiperidine (1.13 g) in dichloromethane (10 ml) were added a solution of 4-fluorobenzoyl chloride (0.99 g) in dichloromethane (1 ml) and diisopropylethylamine (1.09 ml) under cooling on an ice-water bath. The mixture was warmed to ambient temperature slowly under stirring. The mixture was diluted with dichloromethane and washed with water, saturated aqueous sodium hydrogen carbonate, water, and brine. After drying with magnesium sulfate, the solvents were removed under reduced pressure. A residue was purified by column chromatography (silica gel 100 ml, dichloromethane:methanol= 15:1). After rinse with diisopropyl ether-n-hexane (1:1), N-(1-benzylpiperidin-4-yl)-4-fluorobenzamide (1.31 g) was obtained.

NMR (DMSO-d$_6$, δ): 1.4–1.7 (2H, m), 1.7–1.9 (2H, m), 2.01 (2H, br t, J=10.7 Hz), 2.81 (2H, br d, J=11.6 Hz), 3.46 (2H, s), 3.73 (1H, m), 7.2–7.4 (7H, m), 7.90 (2H, dd, J=5.6, 8.9 Hz), 8.26 (1H, br d, J=7.7 Hz); MASS (APCI)(m/z): 313.

Preparation 8

The following compound was obtained by using 4-amino-1-benzylpiperidine as a starting compound according to a similar manner to that of Example 2.

N-(-Benzylpiperidin-4-yl)-N'-(4-fluorophenyl)urea NMR (DMSO-d$_6$, δ): 1.25–1.5 (2H, m), 1.7–1.9 (2H, m), 2.0–2.2 (2H, m), 2.65–2.8 (2H, m), 3.4–3.6 (3H, m), 6.07 (1H, d, J=7.6 Hz), 7.05 (2H, t, J=9 Hz), 7.2–7.45 (2H, m), 8.35 (1H, s); MASS (APCI)(m/z): 328.

Preparation 9

To a solution of N-(1-benzylpiperidin-4-yl)-N'-(4-fluorophenyl)urea (3.0 g) in a mixture of methanol (15 ml) and tetrahydrofuran (15 ml) was added palladium on carbon (10% w/w, 50% wet, 0.6 g), and the mixture was hydrogenated under atmospheric pressure of hydrogen for 8 hours. The catalyst was filtered off, and the solvents were evaporated under reduced pressure to give a residue, which was triturated with diisopropyl ether to give N-(piperidin-4-yl)-N'-(4-fluorophenyl)urea (1.97 g).

NMR (DMSO-d$_6$, δ): 1.1–1.4 (2H, m), 1.65–1.85 (2H, m), 2.3–2.65 (2H, m), 2.8–3.0 (2H, m), 3.3–3.7 (1H, m), 6.08 (1H, d, J=8 Hz), 7.04 (2H, t, J=9 Hz), 7.25–7.5

NMR (DMSO-d$_6$, δ): 1.1–1.4 (2H, m), 1.65–1.85 (2H, m), 2.3–2.65 (2H, m), 2.8–3.0 (2H, m), 3.3–3.7 (1H, m), 6.08 (1H, d, J=8 Hz), 7.04 (2H, t, J=9 Hz), 7.25–7.5 (2H, m), 8.33 (1H, s); MASS (APCI)(m/z): 238.

Preparation 10

A mixture of N-(1-benzylpiperidin-4-yl)-4-fluorobenzamide (937 mg) and 10% palladium on carbon (50% wet, 0.2 g) in methanol (20 ml) was stirred under hydrogen atmosphere for 7.5 hours at ambient temperature. The catalyst was removed by glass filter and the solvent was removed under reduced pressure. After rinse with diisopropyl ether, N-(piperidin-4-yl)-4-fluorobenzamide (653 mg) was obtained.

NMR (DMSO-d$_6$, δ): 1.40 (2H, ddd, J=4.0, 11.9, 23.8 Hz), 1.72 (2H, br d, J=9.5 Hz), 2.3–2.7 (2H, m), 2.8–3.2 (2H, m), 3.80 (1H, m), 7.27 (2H, t, J=8.9 Hz), 7.92 (2H, dd, J=5.6, 8.9 Hz), 8.26 (1H, d, J=7.7 Hz); MASS (APCI)(m/z): 223.

EXAMPLE 1

To a solution of O-phenyl N-(4-pyridyl)carbamate (446 mg) in 1,2-dichloroethane (5 ml) was added a suspension of 1-acetylpiperazine (1.12 g) in 1,2-dichloroethane (20 ml) at ambient temperature. The mixture was heated at 60° C. with stirring for 9 hours. The mixture was cooled to ambient temperature, and diluted with dichloromethane and water. The aqueous phase was separated and adjusted to pH 11.5 with sodium hydroxide solution. Excess sodium chloride was added to the aqueous solution. The mixture was extracted with a mixture of dichloromethane and methanol (about 10:1) and the organic phase was washed with brine. After drying with magnesium sulfate, the solvents were removed under reduced pressure. A residue was purified by column chromatography (silica gel 100 ml, dichloromethane:methanol aqueous ammonia=10:1:0.1). After rinse with diisopropyl ether, 1-acetyl-4-(4-pyridylaminocarbonyl)piperazine (398 mg) was obtained.

NMR (DMSO-d$_6$, δ): 2.03 (3H, s), 3.3–3.6 (8H, m), 7.47 (2H, dd, J=1.5, 4.8 Hz), 8.31 (2H, dd, J=1.5, 4.8 Hz), 9.01 (1H, s); MASS (APCI)(m/z): 271.

EXAMPLE 2

To a stirred solution of 1-acetylpiperazine (0.648 g) in tetrahydrofuran (10 ml) was added 4-fluorophenyl isocyanate (0.574 g) at ambient temperature. After stirring at ambient temperature for 1 hour, the solvent was removed by evaporation under reduced pressure, and the residue was triturated with diisopropyl ether to give 1-acetyl-4-(4-fluorophenylcarbamoyl)piperazine (1.25 g).

NMR (DMSO-d$_6$, δ): 2.03 (3H, s), 3.3–3.6 (8H, m), 7.07 (2H, t, J=9 Hz), 7.46 (2H, dd, J=5, 9 Hz), 8.61 (1H, s); MASS (APCI)(m/z): 266.

EXAMPLE 3

The following compound was obtained by using 1-tert-butoxycarbonylpiperazine as a starting compound according to a similar manner to that of Example 2.

1-tert-Butoxycarbonyl-4-(4-fluorophenylcarbamoyl)-piperazine

NMR (DMSO-d$_6$, δ): 1.42 (9H, s), 3.25–3.5 (8H, m), 7.07 (2H, t, J=9 Hz), 7.45 (2H, dd, J=5, 9 Hz), 8.60 (1H, s); MASS (LD)(m/z): 346.2.

EXAMPLE 4

To a solution of pyridine-4-carboxylic acid (1.0 g) and triethylamine (1.2 ml) in toluene (20 ml) was added diphenylphosphoryl azide (1.75 ml) at ambient temperature. The resulting mixture was heated to reflux for 30 minutes and cooled to 0° C. To the mixture was added 1-tert-butoxycarbonylpiperazine (1.51 g), and the mixture was allowed to heat to 90° C. for 1 hour. After cooling to ambient temperature, the reaction mixture was taken up into ethyl acetate, washed in turn with water and brine, dried over magnesium sulfate, and evaporated under reduced pressure.

The residue was chromatographed on silica gel (150 ml) eluting with 0–7% methanol in dichloromethane. Trituration with a mixture of diisopropyl ether and ethanol gave 1-tert-butoxycarbonyl-4-(pyridin-4-ylcarbamoyl)piperazine (0.66 g).

NMR (DMSO-$d_6$, $\delta$): 1.42 (9H, s), 3.25–3.5 (8H, m), 7.46 (2H, d, J=1.5, 5 Hz), 8.30 (2H, d, J=1.5, 5 Hz), 9.00 (1H, s); MASS (LD)(m/z): 307.2.

EXAMPLE 5

To a suspension of 1-acetyl-4-aminopiperidine hydrochloride (0.4 g) in dichloromethane (5 ml) were added in turn pyridine (0.54 ml) and 4-fluorophenyl chloroformate (0.29 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give 1-acetyl-4-(4-fluorophenoxycarbonylamino)piperidine (347 mg).

NMR (DMSO-$d_6$, $\delta$): 1.15–1.55 (2H, m), 1.7–1.95 (2H, m), 2.00 (3H, s), 2.65–2.85 (1H, m), 3.0–3.25 (1H, m), 3.5–3.7 (1H, m), 3.7–3.9 (1H, m), 4.15–4.3 (1H, m), 7.05–7.3 (4H, m), 7.86 (1H, d, J=8 Hz); MASS (APCI)(m/z): 281.

EXAMPLE 6

To a suspension of 1-acetyl-4-aminopiperidine hydrochloride (715 mg) in dichloromethane (7 ml) were added diisopropylethylamine (1.83 ml) and a solution of 4-fluorobenzoyl chloride (0.83 mg) in dichloromethane (2 ml) at ambient temperature. After stirring for 6.5 hours, the reaction mixture was diluted with dichloromethane and washed with water, saturated aqueous sodium hydrogen carbonate, and brine. After drying with magnesium sulfate, the solvents were removed under reduced pressure. A residue was purified by column chromatography (silica gel 50 ml, dichloromethane:methanol=50:1 to 10:1). After rinse with diisopropyl ether, N-(1-acetylpiperidin-4-yl)-4-fluorobenzamide (738 mg) was obtained.

NMR (DMSO-$d_6$, $\delta$): 1.40 (2H, m), 1.81 (2H, distorted t, J=12.4 Hz), 2.01 (3H, s), 2.68 (1H, br t, J=11.4 Hz), 3.13 (1H, br t, J=11.6 Hz), 3.83 (1H, br t, J=13.9 Hz), 4.01 (1H, m), 4.33 (1H, br d, J=13.7 Hz), 7.29 (2H, t, J=8.9 Hz), 7.92 (2H, dd, J=5.5, 8.8 Hz), 8.31 (1H, d, J=7.7 Hz); MASS (APCI)(m/z): 265.

EXAMPLE 7

To a suspension of 1-acetyl-4-aminopiperidine hydrochloride (536 mg) in dichloromethane (5 ml) were added isonicotinoyl chloride hydrochloride (534 mg) and diisopropylethylamine (1.05 ml) at ambient temperature. After stirring for 8 hours, the reaction mixture was poured into water and diluted with dichloromethane. The mixture was adjusted to pH 8.5 with 1N sodium hydroxide solution. Sodium chloride was added to the mixture and an organic phase was separated. The aqueous phase was extracted with dichloromethane and a combined organic phase was dried over magnesium sulfate. The solvents were removed under reduced pressure. A residue was purified by column chromatography (silica gel 50 ml, dichloromethane:methanol=10:1). After crystallization from diisopropyl ether:n-hexane, N-(1-acetylpiperidin-4-yl)-N-isonicotinamide (477 mg) was obtained.

NMR (DMSO-$d_6$, $\delta$): 1.4 (2H, m), 1.83 (2H, distorted t, J=11Hz), 2.01 (3H, s), 2.69 (1H, br t, J=11Hz), 3.14 (1H, br t, J=12 Hz), 3.83 (1H, br d, J=14.1 Hz), 4.03 (1H, m), 4.33 (1H, br d, J=13.1 Hz), 7.75 (2H, dd, J=1.7, 4.4 Hz), 8.62 (1H, d, J=7.5 Hz), 8.72 (2H, dd, J=1.6, 4.4 Hz); MASS (APCI)(m/z): 248.

EXAMPLE 8

To a suspension of 1-acetyl-4-aminopiperidine hydrochloride (715 mg) in dichloromethane (7 ml) were added diisopropylethylamine (1.83 ml) and a solution of 4-fluorobenzenesulfonyl chloride (0.83 mg) in dichloromethane (2 ml) at ambient temperature. After stirring for 6.5 hours, the reaction mixture was diluted with dichloromethane and washed with water, saturated aqueous sodium hydrogen carbonate, and brine. After drying with magnesium sulfate, the solvents were removed under reduced pressure. A residue was purified by column chromatography (silica gel 50 ml, dichloromethane:methanol=50:1 to 20:1). After rinse with diisopropyl ether, N-(1-acetylpiperidin-4-yl)-4-fluorobenzenesulfonamide (859 mg) was obtained.

NMR (DMSO-$d_6$, $\delta$): 1.21 (2H, m), 1.54 (2H, m), 1.94 (3H, s), 2.66 (1H, br t, J=10.8 Hz), 3.02 (1H, dt, J=2.9, 12.0 Hz), 3.22 (1H, m), 3.64 (1H, br d, J=14.0 Hz), 4.05 (1H, br d, J=13.2 Hz), 7.44 (2H, t, J=8.9 Hz), 7.8–8.0 (3H, m); MASS (APCI)(m/z): 301.

EXAMPLE 9

To a solution of O-phenyl N-(4-pyridyl)carbamate (0.81 g) in chloroform (10 ml) were added 1-acetyl-4-aminopiperidine hydrochloride (0.68 g) and triethylamine (1.06 ml) at ambient temperature. After stirring for 1 day, the mixture changed to a solution. The solvents were removed under reduced pressure. A residue was purified by column chromatography (silica gel 100 ml, dichloromethane:methanol=10:1 to 5:1, and silica gel 50 ml, dichloromethane:methanol:aqueous ammonia=10:1:0.1). The solvents of desired fractions were removed under reduced pressure. A residue was dissolved with methanol (5 ml) and dichloromethane (5 ml), and 4N hydrogen chloride in dioxane (1.5 ml) was added to the solution. The solvents were removed under reduced pressure, and the residue was evaporated azeotropically with methanol. After crystallization from diisopropyl ether and n-hexane, N-(1-acetylpiperidin-4-yl)-N'-(4-pyridyl)urea (343 mg) was obtained.

NMR (DMSO-$d_6$, $\delta$): 1.1–1.6 (2H, m), 1.77 (2H, m), 2.01 (3H, s), 2.94 (1H, br t, J=10.4 Hz), 3.22 (1H, br t, J=10.1 Hz), 3.76 (2H, m), 4.05 (1H, d, J=13.6 Hz), 7.60 (1H, d, J=7.8 Hz), 7.83 (2H, d, J=6.8 Hz), 8.52 (2H, d, J=7.1 Hz), 11.21 (1H, s), 14.66 (1H, br s); MASS (APCI)(m/z): 263.

EXAMPLE 10

To a suspension of 1-acetyl-4-aminopiperidine hydrochloride (536 mg) in dichloromethane (5 ml) were added 4-fluorophenyl isocyanate (375 µl) and diisopropylethylamine (575 µl) at ambient temperature. After stirring for 3 hours, the reaction mixture was diluted with dichloromethane. An organic phase was separated and an aqueous phase was extracted with dichloromethane. A combined organic phase was dried over magnesium sulfate and the solvents were removed under reduced pressure. After crystallization from diisopropyl ether and n-hexane, N-(1-acetylpiperidin-4-yl)-N'-(4-fluorophenyl)urea (448 mg) was obtained.

NMR (DMSO-$d_6$, δ): 1.1–1.5 (2H, m), 1.80 (2H, distorted t, J=10Hz), 2.00 (3H, s), 2.77 (1H, br d, J=10.8 Hz), 3.14 (1H, br d, J=1.1Hz), 3.5–3.9 (2H, m), 4.16 (1H, br d, J=13.2 Hz), 6.15 (1H, d, J=7.6 Hz), 7.05 (2H, t, J=8.9 Hz), 7.40 (2H, dd, J=5.0, 9.2 Hz), 8.37 (1H, s); MASS (APCI)(m/z): 280.

EXAMPLE 11

To a solution of 4-(4-fluorobenzoylamino)piperidine (0.25 g) in dichloromethane (5 ml) were added in turn pyridine (0.14 ml) and methyl chloroformate (87 µl) at 0° C. The mixture was allowed to warm to ambient temperature and stirred for 1 hour. To the mixture was added N,N-dimethylaminopyridine (0.13 g) and allowed to stir for another 1 hour. The reaction mixture was taken up into a mixture of water and ethyl acetate. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give 4-(4-fluorobenzoylamino)-1-methoxycarbonylpiperidine (0.265 g).

NMR (DMSO-$d_6$, δ): 1.3–1.6 (2H, m), 1.75–1.9 (2H, m), 2.8–3.05 (2H, m), 3.60 (3H, s), 3.85–4.1 (2H, m), 7.29 (2H, t, J=9 Hz), 7.90 (2H, dd, J=6, 9 Hz), 8.30 (1H, d, J=8 Hz); MASS (APCI)(m/z): 281.

EXAMPLE 12

To a solution of 4-(4-fluorobenzoylamino)piperidine (0.25 g) in pyridine (5 ml) were added in turn 4-trifluorobenzenesulfonyl chloride (0.219 g) and catalytic amount of N,N-dimethylaminopyridine at 0° C. The mixture was allowed to warm to ambient temperature and stirred for 1 hour, which was taken up into a mixture of water and dichloromethane. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give 4-(4-fluorobenzoylamino)-1-(4-rifluorophenylsulfonyl)-piperidine (0.38 g).

NMR (DMSO-$d_6$, δ): 1.45–1.7 (2H, m), 1.8–1.95 (2H, m), 2.35–2.55 (2H, m), 3.5–3.85 (3H, m), 7.28 (2H, t, J=9 Hz), 7.50 (2H, t, J=9 Hz), 7.75–7.95 (4H, m), 8.31 (1H, d, J=8 Hz); MASS (APCI)(m/z): 381.

EXAMPLE 13

To a solution of 4-(4-fluorobenzoylamino)piperidine (0.15 g) in dichloromethane (5 ml) were added in turn pyridine (82 µl) and 4-trifluoromethoxybenzoyl chloride (106 µ) at 0° C. The mixture was allowed to warm to ambient temperature and stirred for 4 hours, which was taken up into a mixture of water and dichloromethane. The separated organic layer was washed in turn with hydrochloric acid (1N), aqueous sodium hydrogen carbonate, and brine, and dried over magnesium sulfate. Evaporation of the solvent under reduced pressure gave 4-(4-fluorobenzoylamino)-1-(4-trifluoromethoxybenzoyl)piperidine (205 mg).

NMR (DMSO-$d_6$, δ): 1.3–1.7 (2H, m), 1.7–2.0 (2H, m), 2.7–3.4 (2H, m), 3.4–3.8 (1H, m), 3.9–4.2 (1H, m), 4.2–4.6 (1H, m), 7.30 (2H, t, J=9 Hz), 7.35–7.6 (4H, m), 7.91 (2H, dd, J=6, 9 Hz), 8.35 (1H, d, J=8 Hz); MASS (LD)(m/z): 433.2.

EXAMPLE 14

To a solution of 4-(4-fluorobenzoylamino)piperidine (0.15 g) in dichloromethane (5 ml) were added in turn pyridine (0.14 ml) and methanesulfonyl chloride (96 µl) at 0° C. The mixture was allowed to warm to ambient temperature and stirred for 1 hour. To the mixture was added N,N-dimethylaminopyridine (0.13 g) and allowed to stir for another 1 hour. The reaction mixture was taken up into a mixture of water and dichloromethane. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give 4-(4-fluorobenzoylamino)-1-methylsulfonylpiperidine (0.30 g).

NMR (DMSO-$d_6$, δ): 1.45–1.7 (2H, m), 1.8–2.05 (2H, m), 2.7–2.95 (2H, m), 2.88 (3H, s), 3.5–3.65 (2H, m), 3.8–4.05 (1H, m), 7.30 (2H, t, J=9 Hz), 7.91 (2H, dd, J=6, 9 Hz), 8.36 (1H, d, J=8 Hz); MASS (APCI)(m/z): 301.

EXAMPLE 15

To a solution of N-(piperidin-4-yl)-N'-(4-fluorophenyl)urea (0.3 g) in tetrahydrofuran (4 ml) were added in turn pyridine (0.28 ml), methyl chloroformate (98 µl) and catalytic amount of N,N-dimethylaminopyridine at 0° C. The mixture was allowed to warm to ambient temperature and stirred for 2 hours. The reaction mixture was taken up into a mixture of water and ethyl acetate. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give N-(1-methoxycarbonylpiperidin-4-yl)-N'-(4-fluorophenyl)urea (0.312 g).

NMR (DMSO-$d_6$, δ): 1.1–1.4 (2H, m), 1.7–1.9 (2H, m), 2.8–3.1 (2H, m), 3.5–3.75 (1H, m), 3.59 (3H, s), 3.75–3.95 (2H, m), 6.15 (1H, d, J=7.6 Hz), 7.05 (2H, t, J=9 Hz), 7.37 (2H, dd, J=5, 9 Hz), 8.37 (1H, s); MASS (APCI)(m/z): 296.

EXAMPLE 16

To a solution of N-(piperidin-4-yl)-N'-(4-fluorophenyl)urea (0.3 g) in tetrahydrofuran (4 ml) were added in turn N,N-dimethylaminopyridine (0.23 g) and 4-fluorobenzenesulfonyl chloride (0.25 g) at 0° C. The mixture was allowed to warm to ambient temperature and stirred for 1 hour. The reaction mixture was taken up into a mixture of water and dichloromethane. The separated organic layer was washed in turn with hydrochloric acid (1N), aqueous sodium hydrogen carbonate, and brine, and dried over magnesium sulfate. Evaporation under reduced pressure gave a residue, which was triturated with diisopropyl ether to give N-(1-(4-fluorophenylsulfonyl)-piperidin-4-yl)-N'-(4-fluorophenyl)urea (0.468 g).

NMR (DMSO-$d_6$, δ): 1.3–1.6 (2H, m), 1.75–1.95 (2H, m), 2.45–2.7 (2H, m), 3.35–3.6 (3H, m), 6.14 (1H, d, J=7.5 Hz), 7.03 (2H, t, J=9 Hz), 7.34 (2H, dd, J=5, 9 Hz), 7.50 (2H, t, J=9 Hz), 7.75–7.95 (2H, m), 8.31 (1H, s); MASS (APCI)(m/z): 396.

EXAMPLE 17

To a suspension of N-(piperidin-4-yl)-4-fluorobenzamide (0.5 g) in dichloromethane (5 ml) were added pyridine (218 µl), dichloromethane (5 ml) and benzoyl chloride (290 µl) at ambient temperature. After stirring for 3.5 hours, water (5 ml) was poured into the mixture. An organic layer was separated, and washed with water and brine. After drying with magnesium sulfate, the solvents were removed under reduced pressure. A residue was purified by column chromatography (silica gel, toluene:ethyl acetate=1:1 to ethyl acetate). After rinse with diisopropyl ether, N-(1-benzoylpiperidin-4-yl)-4-fluorobenzamide (515 mg) was obtained.

NMR (DMSO-$d_6$, δ): 1.50 (2H, br s), 1.85 (2H, br s), 2.8–3.3 (2H, m), 3.61 (1H, m), 4.1 (1H, m), 4.35 (1H, m), 7.29 (2H, t, J=8.9 Hz), 7.3–7.5 (5H, m), 7.92 (2H, dd, J=5.6, 8.9 Hz), 8.34 (1H, d, J=7.9 Hz); MASS (APCI)(m/z): 327.

EXAMPLE 18

To a suspension of N-(piperidin-4-yl)-4-fluorobenzamide (556 mg) in dichloromethane (5 ml) were added pivaloyl chloride (0.37 ml), pyridine (0.24 ml) and N,N-dimethylaminopyridine (25 mg) at ambient temperature. After stirring for 1 day, the mixture was diluted with dichloromethane, and washed with water and brine. After drying with magnesium sulfate, the solvents were removed under reduced pressure. After trituration with diisopropyl ether, N-(1-pivaloylpiperidin-4-yl)-4-fluorobenzamide (305 mg) was obtained.

NMR (DMSO-$d_6$, δ): 1.20 (9H, s), 1.41 (2H, m), 1.7–1.9 (2H, m), 2.91 (2H, br t, J=11.9 Hz), 4.07 (1H, m), 4.27 (2H, br d, J=13.3 Hz), 7.29 (2H, t, J=8.9 Hz), 7.92 (2H, dd, J=5.5, 8.9 Hz), 8.30 (1H, d, J=7.8 Hz); MASS (APCI)(m/z): 329.

EXAMPLE 19

To a suspension of N-(piperidin-4-yl)-4-fluorobenzamide (556 mg) in dichloromethane (6 ml) were added cyclopropanecarboxylic acid (0.20 ml), 1-hydroxybenzotriazole (338 mg) and 1-ethyl-3-(3-dimethylaminopropyl)carbodiimide hydrochloride (480 mg) at ambient temperature. After stirring for 21 hours, the mixture was diluted with dichloromethane, and washed with water, saturated aqueous sodium hydrogen carbonate, and brine. After drying with magnesium sulfate, the solvents were removed under reduced pressure. After crystallization from diisopropyl ether, N-(1-cyclopropylcarbonylpiperidin-4-yl)-4-fluorobenzamide (627 mg) was obtained.

NMR (DMSO-$d_6$, δ): 0.6–0.8 (4H, m), 1.2–1.6 (2H, m), 1.7–2.0 (2H, m), 1.85 (1H, m), 2.72 (1H, m), 3.21 (1H, m), 4.04 (1H, m), 4.30 (2H, m), 7.29 (2H, t, J=8.9 Hz), 7.92 (2H, dd, J=5.6, 8.9 Hz), 8.31 (1H, d, J=7.7 Hz); MASS (APCI)(m/z): 313.

EXAMPLE 20

1-tert-Butoxycarbonyl-4-(4-fluorophenylcarbamoyl)-piperazine (0.30 g) was dissolved in a solution of hydrogen chloride in ethyl acetate (4N, 2 ml), and the solution was stirred at ambient temperature for 1 hour. The solvent was removed by evaporation under reduced pressure to give 1-(4-fluorophenylcarbamoyl)piperazine as a white powder, which was taken up into dichloromethane (3 ml), and to the mixture were added in turn pyridine (0.25 ml), 4-trifluoromethoxybenzoyl chloride (0.146 ml), and catalytic amount of N,N-dimethylaminopyridine. After stirring at ambient temperature for 12 hours, the mixture was washed in turn with hydrochloric acid (0.5N), aqueous sodium hydrogen carbonate, and brine, dried over magnesium sulfate, and evaporated under reduced pressure. The residue was chromatographed on silica gel (50 ml) eluting with 0%–3% methanol in dichloromethane to give 1-(4-fluorophenylcarbamoyl)-4-(4-trifluoromethoxybenzoyl)-piperazine (0.19 g).

NMR (DMSO-$d_6$, δ): 3.2–3.8 (8H, m), 7.08 (2H, t, J=9 Hz), 7.35–7.5 (4H, m), 7.5–7.65 (2H, m); MASS (LD)(m/z): 434.1.

EXAMPLE 21

The following compound was obtained by using methyl chloroformate as a reactive derivative at the carboxy group according to a similar manner to that of Example 20.

1-Methoxycarbonyl-4-(4-fluorophenylcarbamoyl)piperazine NMR (DMSO-$d_6$, δ): 3.3–3.5 (8H, m), 3.62 (3H, s), 7.07 (2H, t, J=9 Hz), 7.44 (2H, dd, J=5, 9 Hz), 8.62 (1H, s); MASS (APCI)(m/z): 282.

EXAMPLE 22

A mixture of N-acetylpiperidine-4-carboxylic acid (514 mg), 1-hydroxybenzotriazole (405 mg), 1-ethyl-3-(3-dimethylaminopropyl)carbodiimide hydrochloride (575 mg) and 4-fluoroaniline (284.2 ml) in dichloromethane (5 ml) was stirred for 18 hours at ambient temperature. The mixture was diluted with dichloromethane and washed with water, saturated aqueous sodium hydrogen carbonate, water, and brine. After drying with magnesium sulfate, the solvents were removed under reduced pressure. A residue was purified by column chromatography (silica gel 40 ml, dichloromethane:methanol=15:1). After trituration with diisopropyl ether, 1-acetyl-4-(4-fluorophenyl)-carbamoylpiperidine (532 mg) was obtained.

NMR (DMSO-$d_6$, δ): 1.3–1.7 (2H, m), 1.8 (2H, m), 2.01 (3H, s), 2.5 (2H, m), 3.05 (1H, br t, J=10.6 Hz), 3.87 (1H, br d, J=14.1 Hz), 4.40 (1H, br d, J=13.1 Hz), 7.12 (2H, t, J=8.9 Hz), 7.61 (2H, dd, J=5.1, 9.1 Hz), 9.96 (1H, s); MASS (APCI)(m/z): 265.

EXAMPLE 23

A solution of 1-acetylpiperazine-4-sulfonyl chloride (0.91 g) in chloroform (10 ml) were added 4-fluoroaniline (0.38 ml) and triethylamine (0.56 ml) at ambient temperature. After stirring for 6 days, the solvents were removed under reduced pressure. A residue was purified by column chromatography (silica gel 100 ml, dichloromethane:methanol= 19:1). After rinse with diisopropyl ether, 1-acetyl-4-(4-fluorophenyl)-sulfamoylpiperazine (716 mg) was obtained.

NMR (CDCl$_3$, δ): 1.97 (3H, s), 3.09 (4H, m), 3.37 (4H, m), 7.20 (4H, m), 10.00 (1H, s); MASS (APCI)(m/z): 302.

EXAMPLE 24

To a solution of O-tert-butyl (1-acetylpiperidin-4-yl) carbamate (0.97 g) in N,N-dimethylformamide (10 ml) was added 60% sodium hydride (0.18 g) at ambient temperature. After stirring for 40 minutes, 4-fluorobenzyl bromide (0.6 ml) was added to the reaction mixture. After additional stirring for 4 hours, the reaction mixture was poured into a mixture of ethyl acetate (50 ml) and water (10 ml). An organic phase was separated and washed with water and brine. After drying with magnesium sulfate, the solvents were removed under reduced pressure. A residue was purified by column chromatography (silica gel 100 ml, toluene-:ethyl acetate=1:1 to 1:2). After crystallization from diisopropyl ether and n-hexane, O-tert-butyl N-(4-fluorobenzyl)-N-(1-acetylpiperidin-4-yl)carbamate (922 mg) was obtained.

NMR (DMSO-$d_6$, δ): 1.35 (9H, br s), 1.3–1.8 (4H, m), 1.95 (3H, s), 2.3–2.6 (1H, m), 2.97 (1H, m), 3.80 (1H, br d, J=15.2 Hz), 4.0 (1H, m), 4.32 (2H, s), 4.2–4.6 (1H, m), 7.0–7.4 (4H, m); MASS (APCI)(m/z): 295.

EXAMPLE 25

To a solution of O-tert-butyl N-(4-fluorobenzyl)-N-(1-acetylpiperidin-4-yl)carbamate (0.5 g) in dichloromethane (5 ml) was added 4N hydrogen chloride in dioxane (5 ml). The reaction mixture was diluted with diisopropyl ether and the precipitates were collected by filtration. After drying under reduced pressure, 1-acetyl-4-(4-fluorobenzyl)-aminopiperidine hydrochloride (409 mg) was obtained.

NMR (DMSO-$d_6$+$D_2O$, δ): 1.54 (2H, m), 2.02 (3H, s), 2.0–2.3 (2H, m), 2.4–2.7 (1H, m), 3.04 (1H, br t, J=12.1 Hz), 3.29 (1H, m), 3.9 (1H, m), 4.17 (2H, s), 4.44 (1H, br d, J=13.6 Hz), 7.27 (2H, t, J=8.9 Hz), 7.66 (2H, br t, J=6.8 Hz); MASS (APCI)(m/z): 251.

EXAMPLE 26

To a solution of N-(1-acetylpiperidin-4-yl)-4-fluorobenzamide (529 mg) in N,N-dimethylformamide (5 ml) was added sodium hydride (0.1 g). After stirring for 45 minutes, methyl iodide (623 ml) was added to the solution. After stirring for 45 minutes, the mixture was diluted with ethyl acetate (100 ml) and water (50 ml). An organic phase was separated, and washed with water and brine. After drying with magnesium sulfate, the solvents were removed under reduced pressure. After trituration with diisopropyl ether, N-(1-acetylpiperidin-4-yl)-N-methyl-4-fluorobenzamide (248 mg) was obtained.

NMR (DMSO-$d_6$, δ): 1.65 (4H, m), 2.00 (3H, s), 2.78 (3H, s), 3.8 (1H, m), 4.4 (1H, m), 2.0–4.6 (3H, br m), 7.26 (2H, t, J=8.9 Hz), 7.46 (2H, dd, J=5.6, 8.7 Hz); MASS (APCI)(m/z): 301.

EXAMPLE 27

A suspension of 1-acetylpiperazine (0.627 g), 2-chloro-4'-fluoroacetophenone (0.844 g), and potassium hydrogen carbonate (0.735 g) in acetonitrile (12 ml) was stirred at ambient temperature for 3 days. After removal of the solid by filtration, the filtrate was evaporated under reduced pressure to give a residue, which was chromatographed on silica gel (100 ml) eluting with 0%–5% methanol in dichloromethane. The objective compound of the free form was taken up into ethyl acetate (2 ml) and to the solution was added a solution of hydrogen chloride in ethyl acetate (4N, 2 ml). The resulting precipitate was collected by filtration, washed with diisopropyl ether, and dried in vacuo to give 1-acetyl-4-(4-fluorophenylcarbonylmethyl)-piperazine hydrochloride (1.47 g).

NMR (DMSO-$d_6$, δ): 2.06 (3H, s), 2.95–3.8 (6H, m), 3.9–4.15 (1H, m), 4.2–4.45 (1H, m), 5.13 (2H, s), 7.48 (2H, t, J=9 Hz), 8.09 (2H, dd, J=5, 9 Hz); mass (APCI)(m/z): 265.

What is claimed is:

1. A compound of the formula:

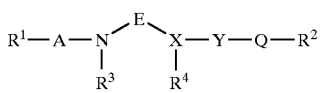 (I)

wherein $R^1$ lower alkanoyl, lower alkoxycarbonyl, benzoyl, benzoyl substituted with halo(lower)alkoxy, lower alkylsulfonyl, phenylsulfonyl, phenylsulfonyl substituted with halogen, or cyclo(lower)alkylcarbonyl;

$R^2$ is phenyl, phenyloxy or phenylamino, each phenyl of which may be substituted with halogen;

A is a single bond;

E is ethylene;

X is CH;

Y is —NH—;

Q is —CO— or —$SO_2$—; and $R^3$ and [4], taken together, form ethylene; and pharmaceutically acceptable salts thereof.

2. The compound according to claim 1, wherein $R^2$ is phenyl which may be substituted with halogen, and Q is carbonyl.

3. The compound according to claim 2, wherein $R^1$ is lower alkanoyl, lower alkoxycarbonyl, benzoyl substituted with halo(lower)alkoxy or cyclo(lower)alkylcarbonyl.

4. A process for preparing a compound of the formula:

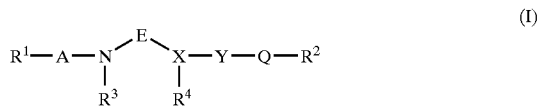 (I)

wherein $R^1$, $R^2$, $R^3$, $R^4$, A, E, Q, X and Y are each as defined in claim 1, or pharmaceutically acceptable salts thereof, which comprises:

(1) reacting a compound of the formula:

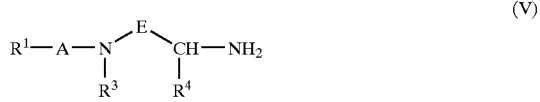 (V)

or its salts with a compound of the formula:

 (III)

or its reactive derivative at the carboxy or sulfo group, or a salt thereof to provide a compound of the formula:

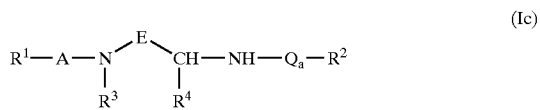 (Ic)

or its salts, in the above formulas $Q_a$ is carbonyl or sulfonyl, and $R^1$, $R^2$, $R^3$, $R^4$, A and E are each as defined in claim 1;

(2) reacting a compound of the formula:

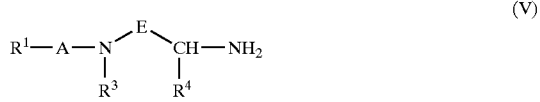 (V)

or its salt with a compound of the formula:

 (IV)

to provide a compound of the formula:

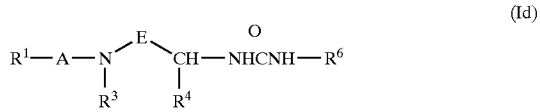 (Id)

or its salt, wherein, in the above formulas, $R^6$ is phenyl which may be substituted with halogen, and $R^1$, $R^3$, $R^4$, A and E are each as defined in claim 1; or (3) reacting a compound of the formula:

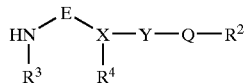  (VI)

or its salt with a compound of the formula:

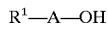  (VII)

or its reactive derivative at the carboxy or sulfo group, or a salt thereof to provide a compound of the formula:

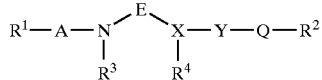  (Id)

or its salt, wherein, in the above formulas, $R^6$ is phenyl which may be substituted with halogen, and $R^1$, $R^3$, $R^4$, A and E are each as defined in claim 1.

5. A pharmaceutical composition, comprising:

a compound of claim 1, as an active ingredient, in association with a pharmaceutically acceptable, substantially non-toxic carrier or excipient.

6. A method for the therapeutic treatment of amnesia, dementia or schizophrenia, comprising:

administering an effective amount of a compound of claim 1 to mammals suffering from amnesia, dementia or schizophrenia.

7. The compound according to claim 2, which is N-(1-acetylpiperidin-4-yl)-4-fluorobenzamide.

* * * * *